(12) United States Patent
Benslimane

(10) Patent No.: US 7,520,896 B2
(45) Date of Patent: Apr. 21, 2009

(54) BREAST IMPLANT, USE OF AN ASSOCIATED POUCH, AND METHOD FOR DETERMINATION OF A BREAST IMPLANT

(76) Inventor: Fahd Benslimane, Impasse Volubilis - Villa No. 9, Avenue de la Côte d'Emeraude, Ain Diab, Casablanca (MA)

( * ) Notice: Subject to any disclaimer, the term of this patent is extended or adjusted under 35 U.S.C. 154(b) by 342 days.

(21) Appl. No.: 10/513,832

(22) PCT Filed: Oct. 28, 2004

(86) PCT No.: PCT/IB2004/003534

§ 371 (c)(1),
(2), (4) Date: Nov. 21, 2005

(87) PCT Pub. No.: WO2006/046091

PCT Pub. Date: May 4, 2006

(65) Prior Publication Data

US 2007/0198085 A1 Aug. 23, 2007

(51) Int. Cl.
*A61F 2/52* (2006.01)
*A61F 2/12* (2006.01)
(52) U.S. Cl. ............................................... 623/7; 623/8

(58) Field of Classification Search ................... 623/7–8
See application file for complete search history.

(56) References Cited

U.S. PATENT DOCUMENTS

| 3,852,832 | A | 12/1974 | McGhan et al. |
| 6,203,570 | B1 * | 3/2001 | Baeke ............................. 623/8 |
| 6,916,339 | B1 * | 7/2005 | Missana et al. ................. 623/8 |
| 2004/0143327 | A1 | 7/2004 | Ku |
| 2004/0249457 | A1 | 12/2004 | Smith et al. |

OTHER PUBLICATIONS

PCT International Search Report for International Application No. PCT/IB2004/003534 (1 page).

* cited by examiner

*Primary Examiner*—Suzette J Gherbi
(74) *Attorney, Agent, or Firm*—Meyertons, Hood, Kivlin, Kowert & Goetzel, P.C.; Eric B. Meyertons

(57) ABSTRACT

The breast implant is tailor-made for a patient and comprises an envelope, which is made in particular of silicone elastomer and inside which a filler product 15 is arranged, and also a securing element 3 disposed on the envelope 2 and intended to be connected to a support element 5, said support element 5 being fixed substantially in the area of the axilla or on the greater pectoral muscle of the patient.

16 Claims, 6 Drawing Sheets

BREAST IMPLANT, USE OF AN ASSOCIATED POUCH, AND METHOD FOR DETERMINATION OF A BREAST IMPLANT

The present invention concerns a breast implant and a method for determination of an implant as a function of a patient's morphology. The invention also relates to the use of a pouch comprising a breast implant.

Breast implants are generally used to increase the volume of a patient's breasts or, in the case of a mastectomy, to reconstruct one of the breasts.

Breast implants generally comprise a molded flexible envelope made of silicone elastomer and forming an interface between the patient and the implant. A filler product, which can be silicone gel or physiological saline, is introduced inside the flexible envelope.

The envelopes are generally produced in what is called a sandwich structure, by successive applications of layers of elastomer inside a mold. Said layers can have different chemical structures and are generally cross-linked. The outer layer of the envelope intended to be in contact with the patient's thorax can undergo surface treatment in order to generate a roughness able to limit movements of the implant during contraction of the capsules, i.e. during cicatrization of the fibrous capsules around the breast implant.

The outer layer of the envelope determines the general shape of the breast implant. Implants generally used are ones having a hemispherical shape, or profiled implants referred to as "anatomical". Such anatomical implants have the advantage of greatly reducing the stepped appearance that can be observed, with hemispherical implants, between said implants and the patient's thorax.

However, such breast implants also have the disadvantage of presenting a particularly unaesthetic visual appearance in the case of movement of the implant, especially during tilting.

The object of the invention is therefore to overcome this disadvantage by making available a breast implant that is able to remain in a desired position after it has been implanted inside a patient's body.

To this end, according to one aspect of the invention, a breast implant tailor-made for a patient comprises an envelope, which is made in particular of silicone elastomer and inside which a filler product is arranged, and a securing element disposed on the envelope and intended to be connected to a support element. Said support element is fixed substantially in the area of the axilla or on the greater pectoral muscle of the patient.

Such a breast implant has the advantage of comprising a securing element with which it is possible to connect the implant, during a surgical intervention, to the axilla or the upper region of the patient's greater pectoral muscle. The support element and the securing element thus make it possible to limit the possible risks of tilting or rotation of the implant, especially during the formation of the fibrous capsules and their cicatrization around the breast implant. In other words, the securing element makes it possible to maintain the desired angular orientation of the breast implant relative to the patient's thorax.

The securing element is situated at the upper end of the implant.

The securing element is preferably attached to the envelope in such a way that at least an upper end part of said element is free, the support element being connected to said securing element in the area of said end part.

The provision of a securing element attached to the envelope favors the use of a material different from that of the envelope and thus being able to present suitable characteristics for permitting fixation of the support element. In addition, an attached element of this kind can substantially simplify the production of the mold from which the breast implant is formed.

Moreover, by virtue of the free upper part, the support element can be easily connected in the area of the securing element, which decreases the risks of contact between the securing element and the envelope of the breast implant, which can generate local deterioration of said envelope.

In one embodiment, the securing element is arranged in the area of the upper end of a posterior portion of the envelope intended to be in contact with the patient's thorax.

The securing element can be substantially offset towards the inside of the envelope in relation to the peripheral edge of the posterior portion.

Such a breast implant has the advantage of comprising a securing element that cannot be felt once the implantation of the breast implant inside the patient's body has been performed.

The envelope preferably comprises at least one adhesive element mounted between a posterior portion of the envelope and the securing element.

Advantageously, the posterior portion of the envelope called the "base" is substantially planar and comprises a main surface which is rounded and substantially circular and continued at an upper end by an end surface of substantially ellipsoid shape, the end surface having a dimension substantially between 20 and 30% of the diameter of the end surface in the area of an axis of symmetry of the breast implant.

The distance between a junction point of the main surface and of the end surface and a straight line passing through the center of the main surface and perpendicular to an axis of symmetry of the envelope can be between 1 and 20% of the diameter of the main surface. In other words, the junction point is a tangential point corresponding to the point of separation between the circular and ellipsoid portions.

Preferably, the angle formed by a vertical line and a tangent of a crossover point between the limit of the end surface and a horizontal line offset upwards relative to the centre of the main surface and situated at a distance equal to half a radius from the centre of the main surface is between 0° and 20°.

Advantageously, the angle formed by a vertical line and a tangent of a crossover point between the limit of the end surface and a horizontal line tangential to an upper end of the main surface is between 23° and 35°.

Preferably, the anterior portion of the envelope comprises a convex lower part having a first radius of curvature determined as a function of the size of the desired implant and continued by a substantially plane upper part. The lower part constitutes the main part of the breast and provides for the projection of said breast and for the increase of its volume. The upper part called the upper continuation makes it possible to provide a smooth transition between the newly enlarged part of the breast and the rest of the chest. This transition zone considerably limits the possible lack of continuity between the newly enlarged breast and the rest of the chest, thus permitting an appearance relatively close to that of a natural breast.

The invention also relates to the use of a breast implant pouch comprising the breast implant and mounted inside a second package, in which the second package of the pouch, being of the same shape as the breast implant, is placed against a patient's thorax, centering it on the nipple of the patient's breast, and the contour of said implant is drawn in order to plot the size of the seat to be created for introducing said implant into the patient's thorax. The invention finally relates to a method for determination and angular orientation of a breast implant as a function of a patient's morphology, comprising steps during which:

the maximum surface of implantation of the breast implant is evaluated on the basis of a first reference distance defined by the spacing between the inframammary fold and a substantially horizontal line passing through the axillae of said patient, and on the basis of a second reference distance defined by the width of the existing breast, and the shape of the breast implant is chosen as a function of the geometry of the surface thus obtained.

Advantageously, a substantially hemispherical breast implant is chosen when the maximum surface of implantation of the breast implant is of square shape and/or a breast implant comprising a posterior portion provided with a circular main surface continued at an upper end by an end surface of substantially ellipsoid shape is chosen when the maximum surface of implantation of the breast implant is of rectangular shape.

In one mode of implementation of the method, having determined the maximum surface of implantation of the breast implant, an ideal minimal surface of said breast implant is determined in such a way that said surface encompasses at least the surface of the existing breast, and a depression formed between the surface of the breast and the projection of the pectoral on the patient's thorax, said minimal surface being centered on the patient's nipple.

Preferably, the axis of orientation and of symmetry of the breast implant is defined as being the axis which is defined by the nipple of the existing breast of the patient and the anterior wall of the axilla of the patient.

The invention and its advantages will be better understood by studying the description of a number of embodiments which are non-limiting and are illustrated by the attached drawings, in which.

Figure 1:
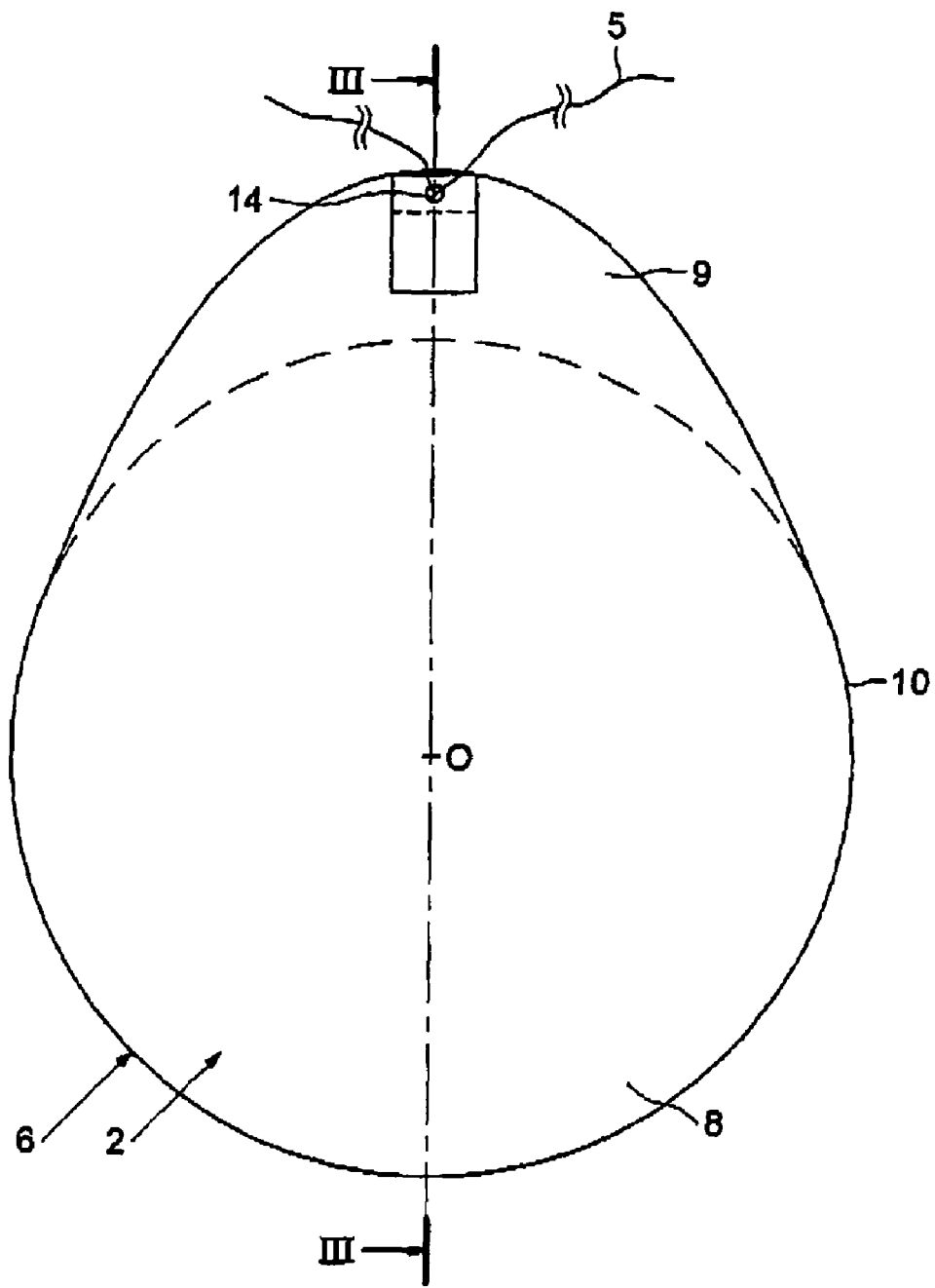
FIG. 1 is a front view of a breast implant according to a first embodiment of the present invention.
Figure 2:
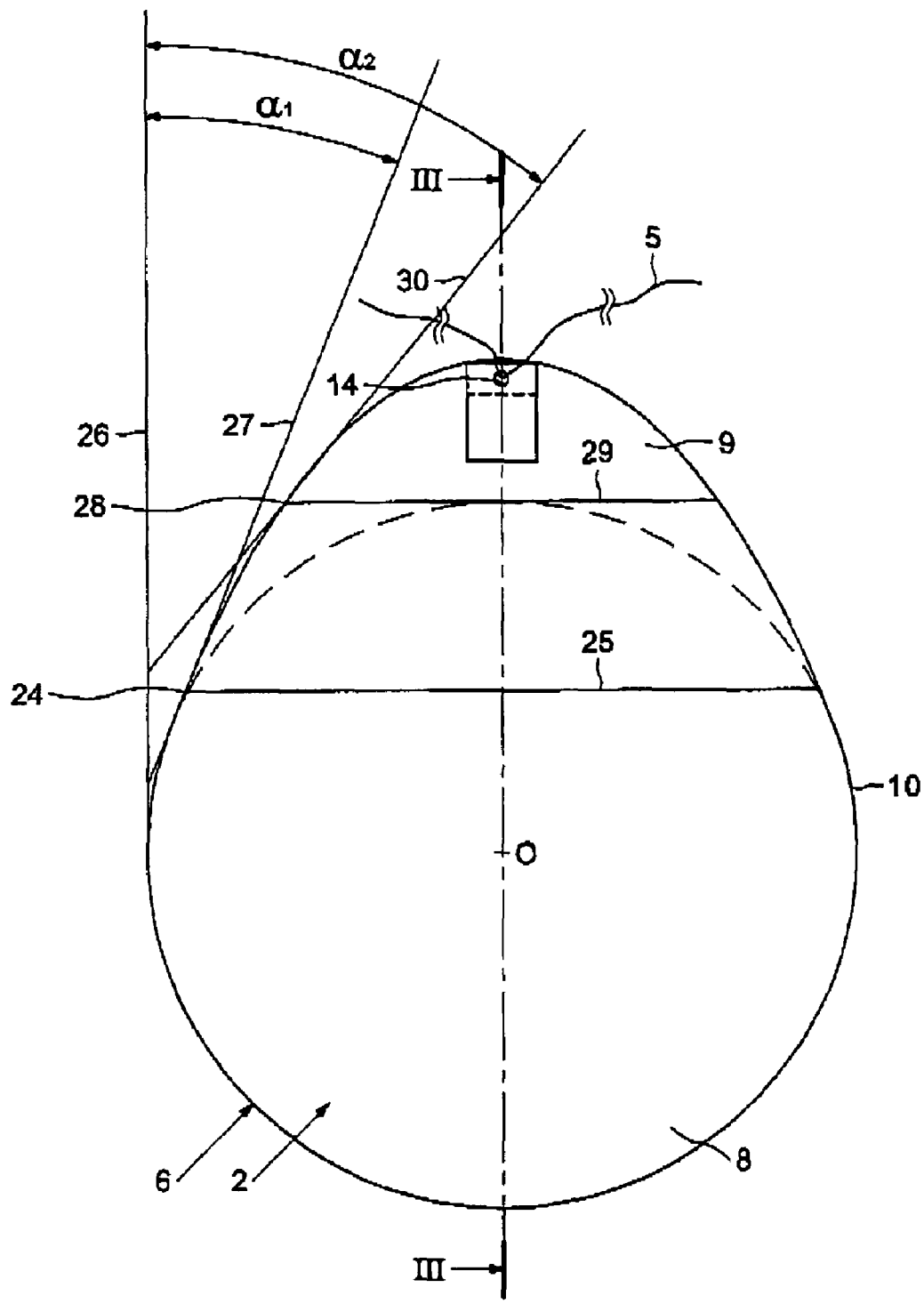
FIG. 2 is a view corresponding to that of FIG. 1, with elements of geometric definition of the breast implant.
Figure 3:
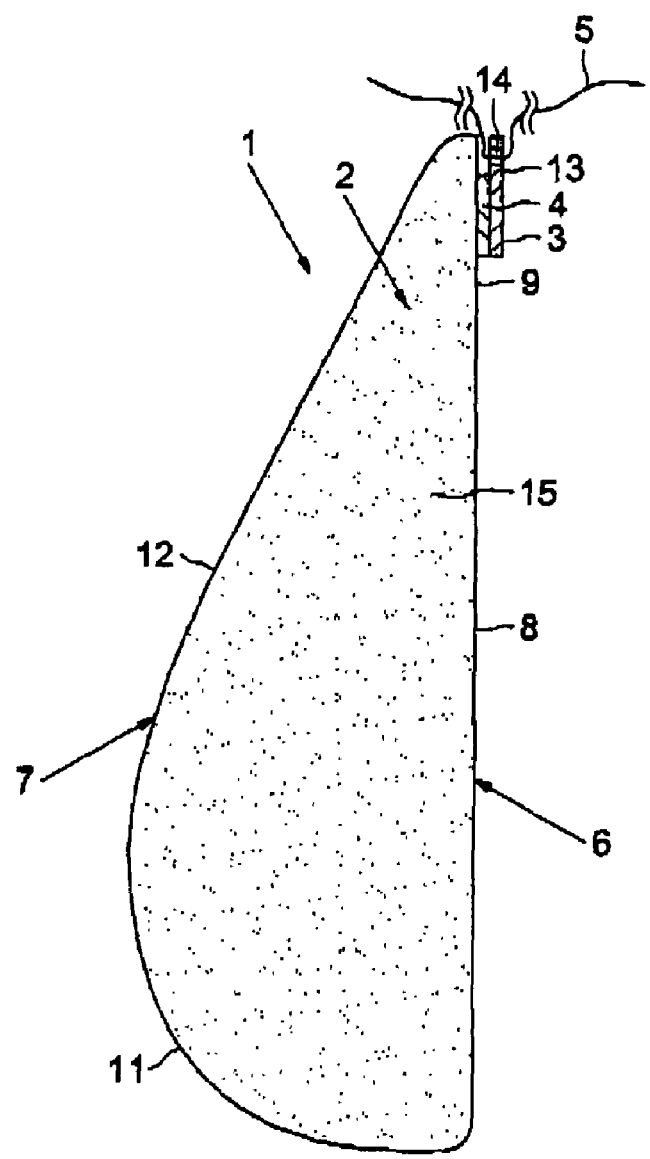
FIG. 3 is a cross section along the axis III-III of the breast implant in FIG. 1.

In FIGS. 1 to 3, the general structure of a breast implant, designated by general reference number 1, has been represented in diagrammatic form. The breast implant 1 comprises an envelope 2, a securing element 3 fixed to the envelope 2 by way of an adhesive element 4, and a support element 5 for maintaining the position of said breast implant 1 connected to the securing element 3.

The envelope 2, for example made of silicone elastomer, has a substantially vertical axis of symmetry coinciding with the axis III-III. It is delimited 20 laterally by a substantially plane posterior portion 6 forming a base, and by a curved anterior portion 7. The posterior portion 6 or base, intended to be in contact with the greater pectoral muscle of a patient (not shown) or the rib cage, is defined geometrically by a circular main surface 8 with center O and a curved end surface 9 substantially in the shape of a crescent. By way of illustration, the continuation of the circular path of the main surface 8 has been shown by a broken line (FIG. 1).

The end surface 9 continues the main surface 8, starting from the upper end of said main surface 8. The term "upper end" is understood here as meaning the part of the main surface 8 nearest to the patient's collar bone when the breast implant 1 is inserted into the patient's body. The end surface 9 forms an axial upward continuation of the main surface. The end surface 9 is defined by an ellipse portion. In the area of the axis of symmetry III-III, it has an axial dimension substantially equal to 20% of the diameter of the main surface 8. Said axial dimension is advantageously between 20 and 30% of the diameter of the main surface 8. The junction point 10 between the main surface 8 and end surface 9 is situated substantially in an upper part of the posterior portion 6 or base. The distance between the junction point 10 and a straight line (not shown) passing through the point O and perpendicular to the axis III-III is preferably between 1 and 20% of the diameter of the main surface 8.

A crossover point 24 is defined by the intersection between the end surface 9 and a horizontal straight line offset upwards in relation to the point O of the main surface 8. The straight line 25 is situated, in relation to the point O, at a distance equal to half a radius of the main surface 8. The angle $\alpha_1$ formed between a vertical straight line 26, parallel to the axis III-III and tangential to the main surface 8, and a tangent 27 to said main surface 8 at the crossover point 24 is between 10° and 20°.

A crossover point 28 is defined by the intersection between the end surface 9 and a horizontal straight line 29 passing through the upper end of the main surface 8. The angle $\alpha_2$ formed between the vertical straight line 26 and a tangent 30 to the main surface 8 at the crossover point 28 is between 23° and 35°.

The anterior portion 7 of the envelope 2 comprises a convex lower part 11 continued upwards, at an upper end, by a substantially plane upper part 12. The lower part 11 is connected to a lower end of the main surface 8 of the posterior portion 6. It has a first radius of curvature $R_1$. The radius of curvature $R_1$ is determined as a function of the size and projection of the desired implant. In other words, the greater the volume of the desired breast implant 1, the more substantial the radius of curvature $R_1$. The upper part 12 forms a continuation of an upper end of the end surface 9 of the posterior portion 6. The upper part 12 is connected to the lower part 11 in the area of a circle portion (not shown). The upper part 12 has a second radius of curvature $R_2$. The second radius of curvature $R_2$ of the upper part 12 has a dimension substantially greater than the radius of curvature $R_1$ of the lower part 11. The upper part 12 can be compared to a plane part and makes it possible to avoid a pronounced transition between the breast implant 1 and the patient's thorax. This is because the distance separating the upper part 12 from the posterior portion 6 is reduced relative to the distance separating the lower part 11 from said posterior portion 6.

The adhesive element 4 is fixed in the area of the base 6 of the envelope 2. The adhesive element 4 is substantially centered relative to the axis III-III and is downwardly offset in relation to an upper end of the end surface 9. The adhesive element 4 here has a substantially rectangular shape. The adhesive element 4 can advantageously be an adhesive made of flexible synthetic material compatible with the material used for the envelope 2, for example a glue.

The securing element 3 is fixed to the adhesive element 4, on the side remote from the envelope 2. The securing element 3, for example made of rigid synthetic material, is arranged partially on the adhesive element 4. In other words, an upper part 13 of the securing element 3 is not attached to the adhesive element 4. An upper end of the free part 13 is substantially flush with an upper end of the posterior portion 6 of the envelope 2. The upper end of the part 13 is thus substantially located in a horizontal plane containing the upper end of the posterior portion 6. The securing element 3 is entirely disposed inside the surfaces 8, 9 of the envelope 2. In other words, the securing element 3 does not protrude from the peripheral edge of the posterior portion 6. The securing element 3 has a relatively small thickness, for example of the order of a millimeter.

The free end part 13 here comprises a circular recess 14 able to permit passage of the support element 5. The support element 5 is here in the form of a thread of flexible synthetic material, for example nylon. It allows the breast implant 1 to be fixed in the area of the patient's axilla and to the upper part of the greater pectoral muscle. Of course, it is also conceivable to provide an adhesive element 4 incorporating the securing element 3, which can be in the form of a loop.

A filler product 15 is arranged inside the envelope 2. The filler product 15 can advantageously be silicone gel or physiological saline. Of course, it is also possible to use another type of product.

Figure 4:
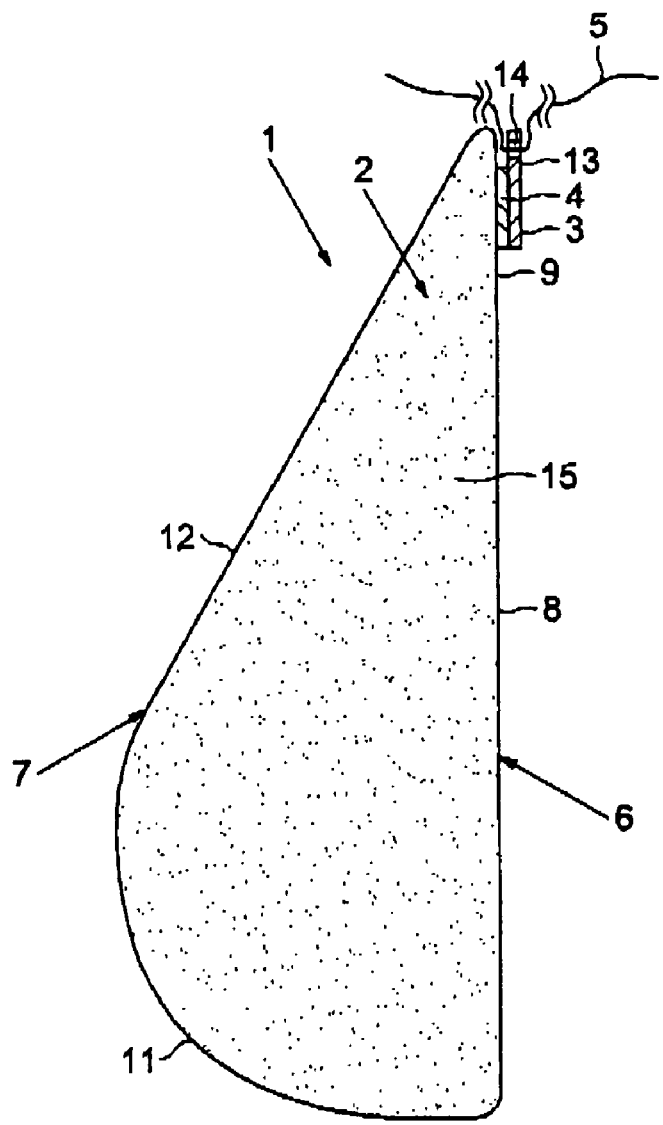
FIG. 4 is a cross section of a breast implant according to a second embodiment of the present invention.

The embodiment illustrated in FIG. 4 differs in that the envelope 2 of the breast implant 1 comprises a plane upper part 12. Analogously to the preceding embodiment, the upper part 12 makes it possible to 25 avoid a pronounced transition between the breast implant 1 and the patient's thorax.

Figure 5:
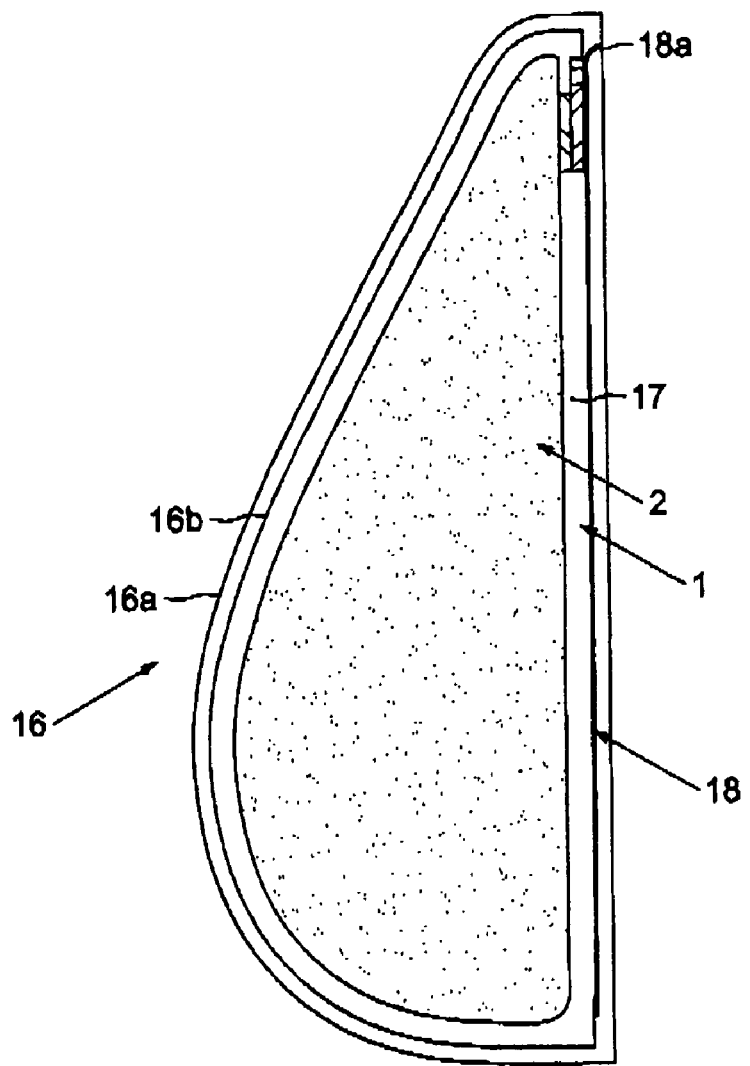
FIG. 5 is a cross section of a pouch according to the present invention for the breast implant in FIG. 1.

FIG. 5 shows a pouch 16 according to the invention and designed in particular to be used as a pouch for the breast implant 1 described above. The pouch 16 can be made of flexible synthetic material and is obtained, for example, by thermoforming. The pouch 16 comprises a first, outer package 16a and a second, inner package 16b inside which the breast implant 1 is placed. The first and second packages 16a and 16b are of a shape corresponding to that of the envelope 2, i.e. the external contour of the packages 16a and 16b is identical to that of the envelope 2. The package 16a comprises an opening 17 permitting passage of the breast implant 1, and of a cover film 18 sealing the opening 17. The cover film 18 here comprises, at a peripheral edge, a tongue 18a for making it easier to remove. The cover film 18 can be made of synthetic material. The package 16a has dimensions slightly greater than that of the envelope 2, for example of the order of a few millimeters. The package 16b has dimensions slightly greater than that of the package 16a, for example of the order of a few millimeters.

Of course, it is also conceivable to provide a pouch 16, for similar purposes, of a shape corresponding to a hemispherical breast implant. The package 16a is sterile and is contained in the non-sterile package 16b. The second package 16b not only makes it possible to avoid contamination of the breast implant 1 by microbes, but can also be used as a stencil for the seat to be created during the surgical intervention, in the area of the patient's thorax, to permit implantation of the breast implant 1.

During the surgical intervention, it is possible to fix such a breast implant 1, by way of the support element 5, by using what is called an axillary route. The axillary route serves uniquely for introduction of the breast implant 1, the dissection being made via an inferior hemi-areolar counterincision. The implant can then be fixed directly to the pectoral muscle.

It is also possible to fix the breast implant 1 using approaches referred to as hemi-areolar, peri-areolar or inframammary. For this purpose, an incision of the order of five millimeters is made, and a curved thread guide is used with which it is possible, in a first stage, to bring a support element 5, in the form of a thread, from the axilla to the approach route, passing through the seat that has been created. This thread is passed through the securing element 3 of the breast implant 1 and then brought back to the axillary incision. The breast implant 1 is then introduced. After the position of the breast implant 1 has been checked, the support element 5 is fixed to the subcutaneous tissue by a counterincision of the axilla and is tied loosely so as to avoid any tension. The aim is to have a support element 5 which then has a long and loose loop permitting a certain play, for example of the order of two centimeters, while at the same time preventing any tilting of the upper pole of the breast implant 1 during cicatrization of the capsules around the envelope 2.

Figure 6:
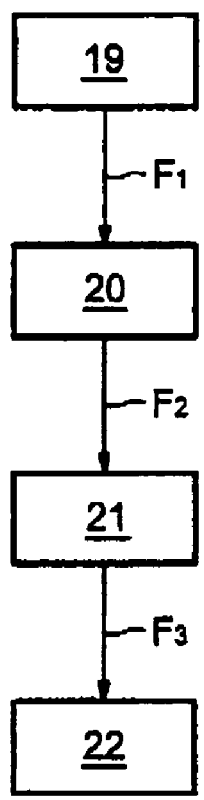
FIG. 6 is a diagrammatic representation of the steps of a method for determination and angular orientation of a breast implant according to the present invention.

FIG. 6 shows the succession of steps involved in a method for determination of a breast implant as function of the morphology of a patient, the arrows $F_1$ to $F_3$ representing the move from one step to the next.

In a first stage, at the step labeled 19, the aim is to determine a maximum area of implantation of the patient's breast implant corresponding to the maximum surface of a posterior portion of the breast implant called "SABIT". For this purpose, in order to evaluate the maximum surface of a posterior portion of the implant, one determines a first, vertical reference distance $d_1$ defined by the spacing between the patient's inframammary fold and a substantially horizontal line passing through the patient's axillae, and a second, horizontal reference distance $d_2$ defined by the width of the existing breast. The maximum surface of implantation is thus delimited in height and in width in the area of the patient's thorax. Advantageously, the contour of this surface is drawn directly on the patient's thorax. If the surface of implantation obtained is square, a hemispherical implant is then chosen. If the surface of implantation obtained is rectangular with a vertical main axis, a breast implant identical to those described above is then chosen. Indeed, to ensure that the posterior portion of the breast implant can uniformly cover the rectangular surface, it is necessary to choose a breast implant, such as those defined above, comprising an end surface of ellipsoid shape corresponding substantially to the axillary continuation of a natural breast, this being commonly referred to as the axillary tail of Spence. It should be noted that in the case when the breast presents an anomaly, for example a constriction of the lower pole, or in the case of a tubular breast, the inframammary fold to be taken into consideration is the one that will exist after implantation of the breast implant, and not the existing fold. In addition, in the case of a tubular breast, the width of the maximum surface of implantation will be calculated not as a function of the width of the base of the existing breast, but as a function of two verticals: one being a medial vertical situated some ten millimeters from the median line, and the other being a lateral vertical running down from the anterior wall of the axilla.

In a second stage, at the step labeled 20, the geometry of the breast implant used can be verified by determining a third reference distance $d_3$ between the patient's collarbone and the inframammary fold, and a fourth reference distance $d_4$ between said inframammary fold and the anterior superior iliac spine. If the distance $d_3$ is less than the distance $d_4$, the inframammary fold is then considered as being situated in a high position on the patient's thorax, and if the distance $d_3$ is greater than the distance $d_4$, the inframammary fold is considered as being situated in a low position. If said distances $d_3$ and $d_4$ are equal to one another, the inframammary fold is then considered as being in a median position.

In the case of an inframammary fold situated in a high position, the maximum surface of implantation is substantially square, which corroborates the choice of a breast implant of hemispherical shape. In the case of an inframammary fold situated in a low position or a median position, said surface is substantially rectangular with a vertical main axis. This step 20 is optional, and it is of course possible to go directly from step 19 to step 21.

In a third stage, after determining the shape of the breast implant to be used and also the maximum surface of implantation of said implant, step 21 involves defining the minimal ideal surface of implantation of the breast implant. For this purpose, the surface needed to encompass at least the surface of the existing breast is determined, and a depression formed between said surface of the existing breast and the projection of the pectoral to the patient's thorax, said necessary surface being centered on the patient's nipple. These elements can, for example, be drawn on the patient's thorax.

Having determined the maximum and minimum surfaces of implantation of the breast implant on the patient's thorax, a breast implant is chosen comprising a posterior portion that has a surface within the range thus defined. The anteroposterior dimension or projection of the breast implant will then be determined according to the patient's wishes so as to obtain reconstructed breasts of greater or lesser volume.

In a fourth stage, in the case of an inframammary fold situated in a low position on the patient's thorax, step 22 involves defining the angular orientation of the breast implant in relation to the thorax. To do this, an anatomical criterion is used according to which a natural breast comprises an axillary continuation, called the tail of Spence, directed towards the armpit. In the case of a surface of implantation of rectangular shape, the axis of orientation of the breast implant is defined by two fixed points: the nipple of the existing breast, on which the breast implant will be centered, and the anterior wall of the patient's axilla.

With the method for determination and orientation of a breast implant, it is thus possible to define the geometric shape of the implant to be used, the surface it will have to cover, and also its angular orientation, in the case of a rectangular geometric figure with a main vertical axis obtained by calculation of a maximum surface of implantation for an inframammary fold situated in a low position. A breast implant having been thus defined, a breast implant pouch can be used to mark, on the patient's skin, the seat that is to be created during the surgical intervention for the purpose of inserting the breast implant in the area of the thorax. The method for determination and orientation of the breast implant, and the use of the breast implant pouch as a stencil for said implant, involve measurements and lines drawn on the patient's thorax in order to determine the dimensions of the breast implant and to visualize the seat to be created, and these procedures do not require the presence of a surgeon.

Furthermore, the breast implant according to the invention comprises a securing element with which it is possible, in a particularly simple and effective manner, to avoid tilting or turning of said implant.

The invention claimed is:

1. Breast implant tailor-made for a patient and comprising an envelope which is made in particular of silicone elastomer and inside which a filler product is arranged, wherein a posterior portion of the envelope is substantially planar and comprises a main surface which is rounded and substantially circular and continued at an upper end by an end surface of substantially ellipsoid shape, the end surface having a dimension substantially between 20 and 30% of the diameter of the main surface in the area of an axis of symmetry of the breast implant.

2. Implant according to claim 1, wherein the distance between a junction point of the main surface and of the end surface and a straight line passing through the center (O) of the main surface and perpendicular to an axis of symmetry of the envelope is between 1 and 20% of the diameter of the main surface.

3. Implant according to claim 1, wherein the angle formed by a vertical line and a tangent of a crossover point between the limit of the end surface and a horizontal line offset upwards relative to the center (O) of the main surface and situated at a distance equal to half a radius from the center of the main surface (8) is between 10° and 20°.

4. Implant according to claim 1, wherein the angle formed by a vertical line and a tangent of a crossover point between the limit of the end surface and a horizontal line tangential to an upper end of the main surface is between 23° and 35°.

5. Implant according to claim 1, wherein an anterior portion of the envelope comprises a convex lower part having a first radius of curvature determined as a function of the size of the desired implant and continued by a substantially plane upper part.

6. Implant according to claim 1, wherein the implant comprises a securing element disposed on the envelope and intended to be connected to a support element, said support element being fixed substantially in the area of the axilla or on the greater pectoral muscle of the patient.

7. Implant according to claim 6, wherein the securing element is attached to the envelope in such a way that at least an upper end part of said element is free, the support element being connected to said securing element in the area of said end part.

8. Implant according to claim 6, wherein the securing element is arranged in the area of the upper end of a posterior portion of the envelope intended to be in contact with the patient's thorax.

9. Implant according to claim 8, wherein the securing element is substantially offset towards the inside of the envelope in relation to the peripheral edge of the posterior portion.

10. Implant according to claim 7, wherein the securing element comprises at least one adhesive element mounted between a posterior portion of the envelope and said securing element.

11. A method of using a breast implant pouch, comprising:
a first package comprising the breast implant and mounted inside a second package, characterized in that the second package of the pouch, being of the same shape as the breast implant, is placed against a patient's thorax, centering it on the nipple of the patient's breast, and the contour of said implant is drawn in order to plot the size of the seat to be created for introducing said implant into the patient's thorax.

12. Method for determination and angular orientation of a breast implant as a function of a patient's morphology, comprising steps during which:
a maximum surface of implantation of the breast implant is evaluated on the basis of a first reference distance defined by the spacing between the inframammary fold and a substantially horizontal line passing through the axillae of said patient, and on the basis of a second reference distance defined by the width of the existing breast, and
the shape of the breast implant is chosen as a function of the geometry of the surface thus obtained.

13. Method according to claim 12, wherein a substantially hemispherical breast implant is chosen when the maximum surface of implantation of the breast implant is of square shape.

14. Method according to claim 12, wherein a breast implant comprising a posterior portion provided with a circular main surface continued at an upper end by an end surface of substantially ellipsoid shape is chosen when the maximum surface of implantation of the breast implant is of rectangular shape.

15. Method according to claim 12, wherein, having determined the maximum surface of implantation of the breast implant, an ideal minimal surface of said breast implant is determined in such a way that said surface encompasses at least the surface of the existing breast, and a depression formed between the surface of the breast and the projection of the pectoral on the patient's thorax, said minimal surface being centered on the patient's nipple.

16. Method according to claim 12, wherein the axis of orientation and of symmetry of the breast implant is defined as being the axis which is defined by the nipple of the existing breast of the patient and the anterior wall of the axilla of the patient.

* * * * *